(12) United States Patent
Trammell

(10) Patent No.: US 7,541,518 B1
(45) Date of Patent: Jun. 2, 2009

(54) ICEBERG LETTUCE PYB 1094

(75) Inventor: Keith W. Trammell, Milwaukie, OR (US)

(73) Assignee: Pybas Vegetable Seed Co., Inc., Santa Maria, CA (US)

( * ) Notice: Subject to any disclaimer, the term of this patent is extended or adjusted under 35 U.S.C. 154(b) by 0 days.

(21) Appl. No.: 12/112,959

(22) Filed: Apr. 30, 2008

(51) Int. Cl.
*A01H 1/00* (2006.01)
*A01H 5/00* (2006.01)
*A01H 5/10* (2006.01)

(52) U.S. Cl. ........................ 800/305; 435/410; 800/260; 800/298

(58) Field of Classification Search ........................ None
See application file for complete search history.

(56) References Cited

U.S. PATENT DOCUMENTS 6,495,744 B2 * 12/2002 Olivas et al. ................ 800/305

* cited by examiner

*Primary Examiner*—David H Kruse
(74) *Attorney, Agent, or Firm*—Haynes and Boone, LLP

(57) ABSTRACT

A lettuce variety with improved resistance to corky root disease is presented. The seed of the lettuce is designated as PYB 1094, a representative sample of which has been deposited under ATCC Accession Number PTA-9155. PYB 1094 is generally early maturing, medium green, and medium-head sized, and shows uniform heading. The invention is also directed to a method of making an F1 hybrid lettuce variety by crossing a plant grown from the seed of PYB 1094 with another plant and selecting a seed from said crossing.

10 Claims, No Drawings

ICEBERG LETTUCE PYB 1094

BACKGROUND

1. Field of Invention

This invention relates generally to the field of plant breeding and particularly to variety of *Lactuca Sativa*.

2. Background

Lettuce is a popular crop that is enjoyed in many parts of the world raw or cooked. As the general population becomes more health-conscious, there is a continued increase of lettuce consumption and a demand for improved varieties. Desired characteristics of a lettuce include round head shape, uniformity, and ease of cultivation.

One of the factors that determine how easy a lettuce variety is to cultivate is its resistance to diseases. One of the common diseases that sabotage lettuce production is corky root, which typically appears as lesions on the root in the beginning. If left uncontrolled, plants infected with corky root will be completely destroyed. In some parts of the country, corky root is known to destroy as much as 50% of the crop. While fumigants such as dazomet, metam sodium and methyl bromide+chloropicrin are known to be effective for controlling corky root, the application of these materials on a commercial scale is undesirably costly.

A lettuce variety that is relatively easy to cultivate on a large scale and has a uniform head shape and appealing size is desired.

SUMMARY

The invention is directed to a lettuce variety with improved resistance to corky root disease. The seed of the lettuce is designated as PYB 1094, a representative sample of which has been deposited under ATCC Accession Number PTA-9155. PYB 1094 is generally early maturing, medium green, and medium-head sized, and shows uniform heading.

The invention is also directed to a method of making an F1 hybrid lettuce variety by crossing a plant grown from the seed of PYB 1094 with another plant and selecting a seed from said crossing.

Other features and aspects of the invention will become apparent from the following detailed description, taken in conjunction with the accompanying drawings which illustrate, by way of example, the features in accordance with embodiments of the invention. The summary is not intended to limit the scope of the invention, which is defined solely by the claims.

DETAILED DESCRIPTION

Also sometimes referred to as "crisphead," an iceberg lettuce forms a tight, dense head that resembles a cabbage. Iceberg lettuces are generally mild in flavor and provide a crunchy texture.

The iceberg lettuce of the invention, named PYB 1094, is an early-maturing, medium green, medium-head-sized iceberg lettuce for mid-spring and summer production in the coastal valleys of California. Besides its early maturity, it is desirable for its uniform heading and resistance to the corky root disease.

Breeding History

The iceberg lettuce PYB 1094 was derived from a cross between Fallgreen and PYB 4601 made in the summer of 1998. PYB 1094 was developed entirely using the well-known pedigree breeding method. The pedigree breeding method is a breeding technique in which the pedigrees of successive generations are recorded and by which successive generations of segregating individual plants are selected following an initial cross. Fallgreen is a lettuce variety suitable for production in the desert southwest. It was released in 1990 as a cross between Emporer and Winterhaven. PYB 4601 is a cross of (Glacier×Pybas 251)×UC 205. Glacier was a corky-root resistant variety released by the USDA in 1991 and was derived from a cross between Green Lake and Salinas. Pybas 251 was a selection from the variety El Toro, and UC 205 was a downy mildew-resistant breeding line from the cross Calmar×Solito released by the University of California, Davis in 1993.

In 1999, F2 seed of the cross between Fallgreen×PYB 4601 was produced in the San Joaquin Valley of California. The seeds were trialed near Santa Maria, Calif. in the summer of 2000. The F2 population was unusually variable with most plants maturing early with a range of head sizes. The heads on many of the plants lacked protection by the outer frame leaves. Two plants with well-formed, large heads and best head protection were selected and self-pollinated to produce F3 seeds. Procedures for self-pollinating lettuces are well known in the art.

In the summer of 2001, the F3 seeds were trialed near Santa Maria, in a field heavily infested with corky root disease. By pulling and examining the root systems of a large number of plants, it was determined that one of the F3 lines was homozygously resistant to corky root. Plants in this line of F3 had clean and healthy tap roots compared to a susceptible check variety. One early maturing plant with a good, round solid head and good coverage was selected and self-pollinated. From this self pollination, F4 seeds were harvested in the fall of 2001.

In late spring of 2002, the F4 seed lot was planted into a trial near Guadalupe, Calif. The population was somewhat variable with head size being medium to large and had shapes varying from round to slightly flattened. As used herein, a "large" head size refers to a diameter measurement of about 18 cm or more, and a "medium" head size refers to a diameter measurement of about 14 cm to about 18 cm. The plot was rather uniformly early maturing. From this plot, five similar plants were selected on the basis of round head shapes and good protection by the outer frame leaves. Later in 2002, F5 seeds were harvested from these selections.

In the spring of 2003, the F5 seed lots were trialed near Guadalupe. Each of the five lines were derived from seeds collected from each of the five plants selected in 2002, respectively. All exhibited the characteristics of early maturity and good head coverage. There was only minimal variation between the lines, mainly for head shape. Five plants that appeared to have the most round heads were selected from the F5 plot and used to produce F6 seeds.

In 2004, the F6 seeds were trialed. Plants grown from the F6 seeds showed excellent uniformity in head shape and size.

In spring of 2005, remnant seed from the single F6 judged to be the best of the trial was planted in the seed production area of the San Joaquin Valley. The seed produced from that sowing was bulked (to produce F7B) and planted in a lot that was trialed in 2006 and 2007. These F7B seeds were used as stock seed for a much larger field increase in 2007.

Characteristics of PYB 1094

| Characteristic | Big Ben | PYB 1094 |
| --- | --- | --- |
| Head Diameter (cm) | 15.97 | 16.25 |
| Head Weight (grams) | 670.15 | 835.65 |
| Core Diameter (cm) | 32.43 | 32.20 |
| Reaction to Corky Root | Resistant | Resistant |

The table above compares PYB 1094 with Big Ben, which is a commercial variety that is similar to PYB 1094.

While the invention has been described in terms of illustration and examples for purposes of clarity and understanding, the description is not intended to be exhaustive or to limit the invention to the precise form disclosed. It should be understood that the invention can be practiced with modification and alteration do not depart from the spirit and scope of the invention as defined by the appended claims.

What is claimed is:

1. A lettuce seed designated as PYB 1094, a representative sample of which has been deposited under ATCC Accession Number PTA-9155.
2. A lettuce plant produced by growing the seed of claim 1.
3. A plant part from the plant of claim 2.
4. A lettuce plant having all of the physiological and morphological characteristics of the lettuce plant of claim 2.
5. A plant part from the plant of claim 4.
6. Pollen of the plant of claim 2.
7. An ovule of the plant of claim 2.
8. A tissue culture of the plant of claim 2.
9. A method of producing lettuce seeds comprising crossing the plant of claim 2 with another lettuce plant and harvesting a seed therefrom.
10. A method of making an F1 hybrid lettuce variety comprising:
    crossing a lettuce plant with a plant grown from the seed of claim 1; and
    selecting a seed from said crossing.

* * * * *